United States Patent
Maletz et al.

(10) Patent No.: US 9,326,917 B2
(45) Date of Patent: May 3, 2016

(54) DENTAL MASKING COMPOUND

(75) Inventors: Reinhard Maletz, Cuxhaven (DE); Wigand Krumme, Cuxhaven (DE); Manfred Thomas Plaumann, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 136 days.

(21) Appl. No.: 13/084,963

(22) Filed: Apr. 12, 2011

(65) Prior Publication Data

US 2012/0093741 A1 Apr. 19, 2012

(30) Foreign Application Priority Data

Apr. 12, 2010 (DE) .......................... 10 2010 003 881

(51) Int. Cl.
*A61K 6/00* (2006.01)
*A61Q 11/00* (2006.01)

(52) U.S. Cl.
CPC ............. *A61K 6/0011* (2013.01); *A61K 6/0017* (2013.01)

(58) Field of Classification Search
USPC ............................... 424/49; 522/83, 171, 173
See application file for complete search history.

(56) References Cited

U.S. PATENT DOCUMENTS

| | | | |
|---|---|---|---|
| 4,369,296 A | 1/1983 | Podszun et al. | |
| 4,490,497 A | 12/1984 | Evrard et al. | |
| 4,507,444 A | 3/1985 | Slawyk et al. | |
| 5,900,245 A | 5/1999 | Sawhney et al. | |
| 6,305,936 B1* | 10/2001 | Jensen et al. | 433/136 |
| 6,800,671 B1 | 10/2004 | Montgomery et al. | |
| 6,964,985 B2* | 11/2005 | Karim et al. | 523/115 |
| 7,789,662 B2 | 9/2010 | Van Eikeren et al. | |
| 2007/0027229 A1* | 2/2007 | Moszner et al. | 523/109 |
| 2007/0142495 A1 | 6/2007 | Neffgen et al. | |
| 2008/0181855 A1* | 7/2008 | Jablow | 424/49 |
| 2010/0152296 A1 | 6/2010 | Marmarinos et al. | |
| 2011/0196056 A1* | 8/2011 | Blackwell | 522/11 |

FOREIGN PATENT DOCUMENTS

| | | | |
|---|---|---|---|
| DE | 1795395 A1 | 1/1972 | |
| DE | 4233886 C1 | 3/1994 | |
| WO | WO 2009/067236 A1 * | 5/2009 | |

OTHER PUBLICATIONS

DeWijn Jr. Reduction of Maximum Temperature in the Polymerization of Cold- and Heat-Curing Acrylic Resins. J. Biomed. Mater. Res. 1974, 8:421-434.*
Sideridou et al ("Effect of chemical structure on degree of conversion in light-cured dimethacrylate-based dental resins." Biomaterials, 2002,2002;23:1819-1829).*
Park, J.-W, et al., "Microhardness of dual-cured composites cured by LED" (presented Jul. 4, 2008 Metro Toronto Convention Centre Exhibit Hall D-E).
Arrais, C.A. Galvão, et al., "Effect of curing mode on the hardness of dual-cured composite resin core build-up materials, " Braz. Oral Res., Apr.-Jun. 2010; 24(2)245-9.
Fonseca, R. Garcia, et al., "The influence of chemical activation on hardness of dual-curing resin cements," Braz. Oral Res, 2004;18(3):228-32.
David C. Watts, "Reaction kinetics and mechanics in photopolymerised networks," Dental Materials (2005) 21, 27-35.
Johannes Steinhaus' Thesis for State Doctoral Exam, "Real-time Investigation of Curing Mechanisms of Thermoset Resins for Medical and Technical Applications," Tomas Bata University in Zlin, Faculty of Technology, Aug. 2013.
Andrzejewska, Ewa, "Photopolymerization kinetics of multifunctional monomers," Prog.Polym. Sci. 26 (2001) 605-665.

* cited by examiner

*Primary Examiner* — Marcos Sznaidman
*Assistant Examiner* — Rayna B Rodriguez
(74) *Attorney, Agent, or Firm* — Duane Morris LLP; Gregory M. Lefkowitz

(57) ABSTRACT

A photopolymerizable dental composition for application to and for the isolation and protection of gums and/or teeth during dental treatment is described. The composition can include (a) one or more photopolymerizable monomers selected from the group consisting of acrylates and methacrylates, (b) one or more photoinitiators, preferably selected from the group consisting of alpha-diketones, benzoin alkyl ethers, thioxanthones, benzophenones, acyl phosphine oxides, acetophenones, ketals, titanocenes, borates and sensitizing dyes, and (c) one or more molecular weight regulators selected from the group consisting of compounds which can be reacted with a radical of a monomer of component (a) with abstraction of an H radical from the molecular weight regulator in the allyl position. Also disclosed are kits comprising such a composition, methods for producing a corresponding protective layer, methods for treating one or more teeth, and methods of using the compositions as a masking compound.

19 Claims, No Drawings

DENTAL MASKING COMPOUND

CROSS REFERENCE TO RELATED APPLICATIONS

This application claims priority to German Patent Application No. DE 10 2010 003 881.4, filed Apr. 12, 2010, the entire contents of which are incorporated herein by reference.

FIELD OF THE INVENTION

The invention relates primarily to a photopolymerizable dental composition for isolating tooth substance to be treated and for protecting the surrounding gums and/or one or more adjacent teeth against dental treatment agents. The invention also relates to a kit comprising such a dental composition, to a method for producing a corresponding protective layer, to a method for treating one or more teeth, and to a corresponding composition as a masking compound.

BACKGROUND OF THE INVENTION

In the context of the present text, a "dental masking compound" according to the invention is understood to mean a photopolymerizable dental composition based on radically curable acrylate/methacrylate systems for application to and for the isolation and protection of gums and/or teeth before and during dental treatment.

There are a number of treatment methods used by dentists in which aggressive chemical substances which may be harmful to health and which may damage the oral mucosa are used in the oral cavity.

For example, during placement of a composite filling, use is made of the so-called "acid etch technique" in which both the enamel and the dentin of a prepared cavity are conditioned to build up adhesion before applying a bonding liquid. The conditioning agent used may be for example phosphoric acid, maleic acid, nitric acid, citric acid or oxalic acid. Nowadays, use is generally made of a 35-40% strength phosphoric acid. In order to be able to obtain a sufficient etch pattern on the prepared enamel, the acid is first left to act on the enamel for 15 seconds and then the acid is applied to the dentin, where it is allowed to act for a further 15 seconds. Before continuing with the treatment, the acid residues are then rinsed off and removed by suction. During this process, the gums as soft tissue must be isolated from the acid residues.

The preparations are often located at the edges of the teeth or at the necks of the teeth. In these cases, the adjacent tooth and/or the soft tissue is in the direct vicinity of the treatment site. Of course, in such cases, the adjacent tooth and/or gums must be protected from the etching agent.

Another method used by dentists, in which the oral cavity comes into contact with aggressive chemical substances, is oxidative tooth whitening, also known as "bleaching", this being a method which has in recent times become an integral part of aesthetic (cosmetic) dental treatment. The whitening effect is in this case achieved by oxidizing agents such as hydrogen peroxide, perborates or carbamide peroxide. Usually, peroxide-containing gels are used.

Enamel and dentin are stained by colorings that have become embedded in the tooth. The peroxides used penetrate into the tooth substance and oxidize the embedded colorings. Colorless fragments are left behind, and stains are removed from enamel and dentin. The reactive species in this process are free radicals which are able to attack and to destroy even the body's own structures. During the whitening of vital teeth, the bleaching agent is applied to the outer tooth surfaces as far as the area of the gingival margin. It is known from early conventional experiments that, in a high percentage of patients, gingival irritation occurred during the bleaching treatment. In order to prevent this irritation, a protective masking of the oral mucosa is necessary.

There are numerous other treatment methods used by dentists in which the treated tooth or even a plurality of treated teeth must be kept in a dry state. To this end, this treatment site must remain shielded in a liquid-tight manner from surrounding hard and soft tissue.

The conventional method for shielding and isolating tooth substance to be treated from the rest of the oral cavity and for protecting vulnerable soft tissue is the so-called "rubber dam technology" which was developed using a tensioned rubber sheet, referred to as the rubber dam. In this technique, the dentist perforates the rubber dam membrane at the appropriate points using a punch and then places the perforated membrane over the tooth to be treated. The rubber dam is then tensioned by means of a rubber dam frame, so that the tooth is shielded from the surrounding oral cavity. There are many disadvantages of the "rubber dam technology". For instance, the patient usually experiences an unpleasant feeling due to the compressive stress of the metal brackets on the tooth. He can no longer close his mouth and has to breathe through the nose. The method is extremely complicated and time-consuming for the dentist and is also highly sensitive to errors during use. For example, if the hole is not punched to the correct size in the rubber sheet, the rubber dam will not sit precisely and in a taut enough manner along the gingival margin and will not provide sufficient sealing. There is also the risk that the sheet may tear during tensioning or during the treatment, so that the shielding effect is lost and for example aggressive chemical substances can pass unhindered to the soft tissue parts of the mouth and may cause damage there.

It is known that, during the radical polymerization of light-curable methacrylate systems, a large quantity of heat is produced and must be dissipated, particularly when such compositions are to be used for example on the soft tissue of the mouth interior. It should be ensured that no pain or even burning can occur as a result of the quantity of heat released in the oral cavity of the patient.

U.S. Pat. No. 6,305,936 B1 proposes compositions based on radically curable methacrylate systems and methods which are said to overcome the above-mentioned disadvantages of the rubber dam technique. To reduce the amount of heat, non-reactive plasticizers such as polyols or mineral oil are used in U.S. Pat. No. 6,305,936 B1. One disadvantage here is for example the fact that the use of non-reactive plasticizers disrupts the process of homogeneous crosslinking and thus may lead to the presence of unreacted monomers. Monomeric methacrylates have cytotoxic properties and may have a sensitizing effect on the tissue.

U.S. Pat. No. 6,800,671 B1 relates to isolation material for isolating tooth substance to be treated and the surrounding gums. The compositions described therein contain unsaturated, curable compounds which have an unsaturation index of at least 500. According to U.S. Pat. No. 6,800,671 B1, preferred curable compounds are dimethacrylate polyether urethane oligomers having molecular weights of between 1000 and 3000 g/mol. In addition to these multifunctionally unsaturated compounds, the compositions described therein contain a curing agent and an adhesion-promoting compound. In order to be able to ensure a workable consistency of the composition, a non-curable diluent such as for example mono-, di- or triglycerides or vegetable oil may be added to the composition of U.S. Pat. No. 6,800,671 B1.

WO 2008/096182 relates to a photopolymerizable material for isolating and for protecting the gums, for example during tooth whitening. The composition described therein comprises at least one monomer, at least one polymerization agent, at least one inert raw material and, as a further component, at least one compound having antioxidant, anti-inflammatory or sedative properties. Tocopheryl acetate, a compound which does not participate in radical polymerization, is used in a quantity of up to 25% by weight in some examples. In the case of the compositions according to WO 2008/096182, it is also to be expected that these do not form homogeneous polymers and that an excessively high quantity of unreacted monomer will be present in the cured material.

U.S. Pat. No. 5,900,245 also provides a system for shielding soft tissue, wherein the tissue surface is coated with a plastic composition. Therein, firstly a polymerization initiator is applied to the tissue surface and then a curable composition is applied to the ready-prepared tissue surface and is cured under light.

EP 1 553 915 B1 discloses the use of an elastomeric masking compound which adheres to the gums and which, as a two-component system, mixed at ambient temperature, crosslinks in a self-curing manner on the tissue to be protected. This system is based on silicone chemistry.

DE 42 33 886 C1 discloses polymerizable conditioning agents based on methacrylate and a method for pre-treating the surface of shaped bodies made from polyacrylate, polymethacrylate and polycarbonate plastics prior to application of polymerizable methacrylate material and use of the conditioning agent. The conditioning agent may contain monocyclic terpene hydrocarbon. A use of the disclosed conditioning agent for isolating tooth substance to be treated and for protecting the surrounding gums and/or one or more adjacent teeth against dental treatment agents is not described; such a use moreover appears to be ruled out due to the use of alkyl methacrylates, which are classified as toxic. DE 30 10 373 A1 discloses methods for polymerizing methacrylic acid methyl esters or mixtures thereof with further vinyl monomers in the presence of enol ethers. The polymers produced by the disclosed method are referred to as being particularly suitable for use in the dental field, for example for producing prostheses according to the powder/liquid method. Not disclosed, however, are compositions which appear to be suitable for producing a (sufficiently elastic and non-toxic) isolation of tooth substance to be treated and protection of the surrounding gums and/or one or more adjacent teeth against dental treatment agents.

DE 27 27 480 A1 discloses impact-resistant, vitreous plastic alloys of polymethacrylates and aliphatic polyurethane ureas. Methods for the production thereof are disclosed, in which use is made of monomer mixtures comprising sulfur-containing molecular weight regulators. Not disclosed are compositions for the dental field and in particular also compositions which appear to be suitable for producing a (sufficiently elastic and non-toxic) isolation of tooth substance to be treated and protection of the surrounding gums and/or one or more adjacent teeth against dental treatment agents.

DE 17 95 395 A discloses methods for producing polymers and copolymers of (meth)acrylic acid esters and acrylonitrile in the presence of polymerization catalysts and compounds having a six-membered ring containing two non-conjugated double bonds, one of which may be semicyclic (exocyclic). The specifically disclosed polymerization catalysts are thermal catalysts; photoinitiators or photopolymerizable dental compositions are not disclosed.

U.S. Pat. No. 4,490,497 A discloses compositions for surgical cement, which can be used in the production of dental prostheses. A liquid component of the composition comprises as the "chain stopper" for example a diunsaturated monocyclic terpene or a monounsaturated bicyclic terpene. Not disclosed are compositions which appear to be suitable for producing a (sufficiently elastic and non-toxic) isolation of tooth substance to be treated and protection of the surrounding gums and/or one or more adjacent teeth against dental treatment agents.

EP 1 720 506 B1 discloses a filled and polymerizable dental material and also a method for the production thereof. As use examples, the following are mentioned: tooth filling materials, core build-up materials, materials for temporary crowns and bridges, dental cement adhesives, materials for artificial teeth, veneering materials, sealing materials and dental varnish. It is disclosed that the dental material may contain additives and/or modifiers in order to set certain properties; a long list of examples includes "terpinenes". Not disclosed, however, are compositions which appear to be suitable for producing a (sufficiently elastic and non-toxic) isolation of tooth substance to be treated and protection of the surrounding gums and/or one or more adjacent teeth against dental treatment agents.

In the systems for the radical polymerization of light-curable compounds, the problem of the considerable development of heat is in all cases tackled either by adding non-reactive additives to the composition and/or by using monomers of high molecular weight, i.e. compounds having a small number of double bonds. The use of substances which do not participate in the crosslinking on the one hand disrupts the homogeneous progress of radical polymerization and moreover, as is known, leads to the compounds not incorporated in the network from migrating out of the organic matrix and possibly damaging the soft tissue. If, on the other hand, monomers of high molecular weight are used, the mobility of the functional groups is reduced and the likelihood that each reactive group will also find an appropriate reaction partner is decreased. The mechanical properties of the protective film are diminished and the quality of the isolation material will suffer.

With the chemically curing systems based on silicone, the crucial advantages are obtained that they are biocompatible and exhibit no development of heat during curing. However, the acceptance of silicones by dentists is not very pronounced since dentists are primarily interested in rapid curing processes delivered by the use of light-curable compounds.

The object of the present invention is therefore to provide a composition for isolating tooth substance to be treated and for protecting the surrounding gums and/or one or more adjacent teeth against dental treatment agents based on light-curable methacrylate/acrylate systems, which is not reliant on the addition of non-reactive additives or the exclusive use of monomers of high molecular weight. Such a material should cure quickly, should not release any compounds not involved in the polymerization to the surrounding tissue, should exhibit high crosslinking rates and thus no longer contain, after curing of the material, any disadvantageous quantities of unreacted monomers which may subsequently have a harmful effect on the tissue, should provide a regularly constructed network and thus exhibit good mechanical properties, should adhere to the tissue and should nevertheless be easily removable.

The object is achieved by a composition according to claim 1. Advantageous embodiments of the invention are indicated in the dependent claims.

The present invention thus relates to a photopolymerizable dental composition for application to and for the isolation and protection of gums and/or teeth during dental treatment, comprising:
(a) one or more photopolymerizable monomers selected from the group consisting of acrylates and methacrylates, preferably from the group of the methacrylates,
(b) one or more photoinitiators, preferably selected from the group consisting of alpha-diketones, benzoin alkyl ethers, thioxanthones, benzophenones, acyl phosphine oxides, acetophenones, ketals, titanocenes, borates and sensitizing dyes,
(c) one or more molecular weight regulators selected from the group consisting of compounds which can be reacted with a radical of a monomer of component (a) with abstraction of an H radical from the molecular weight regulator in the allyl position,
and optionally one or more further additives.

It has surprisingly been found that it is possible to provide light-curable compounds based on photopolymerizable monomers from the group of acrylates and methacrylates in the form of masking compounds for isolating tooth substance to be treated and for protecting the surrounding gums and/or one or more adjacent teeth against dental treatment agents (in particular dental bleaching agents) if the molecular weight regulators to be used according to the invention are added to the compounds. The compositions according to the invention cure quickly, do not release any great quantities of heat to the surrounding area, exhibit high crosslinking rates, preferably do not contain any non-reactive components and preferably do not contain exclusively monomers of high molecular weight.

The compositions according to the invention preferably contain one or more photopolymerizable monomers of low molecular weight, more preferably one or more photopolymerizable monomers having a molecular weight of <700 g/mol, particularly preferably having a molecular weight of <600 g/mol.

In a further preferred embodiment, a composition according to the invention contains a total quantity of photopolymerizable monomers of low molecular weight of more than 50% by weight, relative to the total amount of monomers in a composition according to the invention.

It was surprisingly found that in particular the molecular weight regulators to be used with (particular) preference according to the invention (see below) provide a highly effective regulating effect in a dental masking compound according to the invention. The observed temperature profile of a masking compound according to the invention is reduced in its maximum by several degrees Celsius compared to the temperature development of a formulation with no molecular weight regulator. Given the presence of a suitable molecular weight regulator, the released quantity of heat is not released in an unchecked and uncontrolled manner "in one fell swoop", but rather in a "regulated", i.e. controlled manner, so that high thermal stresses or even burning on the tissue in the oral cavity can be ruled out. At the same time, the regulator must reduce the molecular weight of the polymer so that the material adheres well to the tissue and nevertheless is easily removable.

DETAILED DESCRIPTION

Compared to the prior art, there is thus provided here a masking compound for isolating tooth substance to be treated and for protecting the surrounding gums and/or adjacent teeth against dental treatment agents, which preferably has two, three or all of the following properties:
1.) the masking compound is substantially free, preferably free, of non-reactive organic compounds which can be released to the surrounding area and which stand in the way of a homogeneous build-up of the polymer,
2.) the masking compound cures quickly and homogenously and achieves high reaction rates, wherein the molecular weights of the monomers used lie in an order of magnitude which allows a sufficient mobility of the reactive species, so that it is not to be expected that the cured compound contains disadvantageous quantities of unreacted monomers which may subsequently have a harmful effect on the tissue,
3.) the cured isolation has a homogeneous and regularly constructed network which, compared to a masking compound without any regulator, has a lower molecular weight so that the cured compound has softer properties leading to the situation whereby it adheres to the tissue in a flexible manner with a good mechanical profile and nevertheless can easily be removed,
4.) the masking compound solves the major problem of dental masking compound systems based on methacrylate/acrylate chemistry, namely the release of large quantities of heat, without having to take account of other disadvantages.

Molecular weight regulators (hereinafter also referred to in short as regulators) are known per se and are commercially available. They are used for example in the solution polymerization of olefins, in the emulsion polymerization of methacrylates or for the production of shaped bodies from PMMA molding compounds (PMMA=polymethyl methacrylate) by compression molding or injection molding.

Molecular weight regulators are so-called transfer reagents which enter into transfer reactions in a free radical reaction involving mechanistic H abstraction and transfer of the radical function to the regulator. Due to its function, the regulator can then be found again in the form of end groups in the crosslinked polymer.

Customary regulators are for example aldehydes and ketones, such as formaldehyde, acetaldehyde, propionaldehyde, n-butyraldehyde, isobuty, raldehyde, methyl ethyl ketone, acetone, methyl isobutyl ketone, formic acid, ammonium formate, hydroxyl-ammonium sulfate and hydroxylammonium phosphate, compounds which contain sulfur in organically bound form, such as di-n-butyl sulfide, di-n-octyl sulfide, diphenyl sulfide, diisopropyl disulfide, di-n-butyl disulfide, di-n-hexyl disulfide, diacetyl disulfide and di-tert.-butyl trisulfide, compounds which contain sulfur in the form of SH groups, such as n-butyl mercaptan, n-hexyl mercaptan and n-dodecyl mercaptan, octadecyl mercaptan, further sulfur compounds such as hydrogen sulfites, disulfites, compounds such as mercaptoethanol, mercaptobutanol, mercaptoacetic acid, 3-mercaptopropionic acid, mercaptosuccinic acid, thioglycerol, thioglycolic acid, diethanol sulfide, thiodiglycol, ethylthioethanol, 2,2,4,6,6-pentamethylheptane-4-thiol, 2,2,4,6,6,8,8-heptamethylnonane-4-thiol, thiourea, dimethyl sulfoxide, ethylhexyl thioglycolate, pentaerythritol tetrathioglycolate, mercapto-propyltrimethoxysilane, then allyl compounds such as allyl alcohol, allyl bromide, or benzyl compounds such as benzyl chloride or alkyl halides such as chloroform, bromotrichloromethane or tetrachloromethane, tetrabromomethane, methylene chloride, also low and high molecular weight monovalent or polyvalent alcohols such as methanol, ethanol, n-propanol, isopropanol, tert.-butanol, sec-butanol, n-butanol, amyl alcohol, cyclohexanol, octanol, dodecanol, 1-ethylhexanol, glycerol, stearyl alcohol, oleyl alcohol, hydroxyethyl methacrylate or amines such as triethylamine and toluene or ethylbenzene.

However, the abovementioned regulators are unsuitable for the intended use here. For instance, sulfur-containing molecular weight regulators have an intensive and typically unpleasant odor and separate out as a component of a dental material. It has also been found that low or high molecular weight monovalent or polyvalent alcohols in the compositions do not provide any regulating effect and remain ineffective. The same applies to aldehydes and ketones and also to acids.

The precise reason for the success according to the invention when using the abovementioned molecular weight regulators (c) is not known in detail. Presumably, however, there is a particular, previously unexpected interaction between the monomer(s) and the molecular weight regulator(s), which makes it possible for the molecular weight regulator (c), during the photopolymerization of the masking compound according to the invention, to have an effect on the progress of polymerization in such a way and to such an extent that the chain length, crosslinking and residual monomer content of the polymer being formed are such that the desired properties are obtained.

Molecular weight regulators which are suitable according to the invention are for example various terpenes, in particular terpinenes (α-terpinene, β-terpinene, γ-terpinene), phellandrenes (α-phellandrene, β-phellandrene) and terpinolene (also known as δ-terpinene), 1,4-cyclohexadiene (optionally substituted), 1,3-cyclohexadiene (optionally substituted), 1,4-dihydronaphthalene, 1,4,5,8-tetrahydronaphthalene, 2,5-dihydrofuran or dimeric α-styrene (2,4-diphenyl-4-methyl-1-pentene) as well as linoleic acid and α-linolenic acid.

Molecular weight regulators to be used with preference according to the invention as component (c) in a masking compound according to the invention are compounds having two or more double bonds, preferably compounds having two or more double bonds which, by abstraction of an allyl H atom, can form a delocalized electron system which extends over 5 or more C atoms, preferably dienes which, by abstraction of an allyl H atom, can form a delocalized electron system which extends over 5 C atoms.

Molecular weight regulators to be used with preference according to the invention as component (c) in a masking compound according to the invention are selected from the group of the monoterpenes, preferably from the group of the monoterpene dienes, preferably from the group consisting of α-terpinene, β-terpinene, γ-terpinene, α-phellandrene, β-phellandrene and terpinolene or are selected from the group consisting of linoleic acid, linolenic acid and other substituted or unsubstituted cyclohexadienes.

Regulators which are particularly preferred according to the invention are α-terpinene and γ-terpinene, particular preference being given to γ-terpinene.

Mixtures of molecular weight regulators can of course also be used in a masking compound according to the invention.

The addition of molecular weight regulators, in particular of the molecular weight regulators to be used according to the invention, of component (c) to dental masking compounds is previously unknown.

In EP 1 720 506, WO 2009/083168 A1, DE 10 2008 028 306 A1, EP 1 872 767 A1 and EP 2 070 506, none of which concern masking compounds in the sense of the present invention, terpinenes are mentioned inter alia in the respectively indicated list of stabilizers.

Dental compositions according to the invention preferably comprise no sulfur-containing molecular weight regulators.

Dental compositions which are preferred according to the invention comprise component (a) in a quantity of from 50 to 90% by weight, preferably in a quantity of from 60 to 80% by weight,
component (b) in a quantity of from 0.01 to 1% by weight, preferably from 0.05 to 0.5% by weight, more preferably from 0.1 to 0.3% by weight,
and
component (c) in a quantity of from 0.075 to 7.5% by weight, preferably from 0.125 to 3% by weight, more preferably from 0.2 to 1.5% by weight,
in each case relative to the total weight of the dental composition.

Component (a)—Photopolymerizable Monomers

The radically light-polymerizable monomers may be at least two substances containing ethylenic groups, such as for example, without being limited thereto, the (meth)acrylate monomers usually used in composite materials in dental chemistry.

The patent literature mentions a large number of further compounds (for example including in DE 39 41 629 A1, which by way of reference forms part of the present application), all of which are diesters of acrylic or methacrylic acid and are suitable for use in a composition according to the invention.

In one preferred dental composition according to the invention, component (a) comprises
(a) (i) one or more dimethacrylate monomers
and/or
(a) (ii) one or more acid group-containing monomers,
wherein component (a) preferably comprises both component (a) (i) and (a) (ii).

In one preferred dental masking compound according to the invention, component (a) (i) contains one or more dimethacrylate monomers selected from the group consisting of ethylene glycol dimethacrylate (EGDMA), 1,6-hexanediol dimethacrylate (HEDMA), triethylene glycol dimethacrylate (TEGDMA), 1,12-dodecanediol dimethacrylate (DODMA), ethoxylated bisphenol A dimethacrylate, polyethylene glycol dimethacrylate (PEGDMA), 7,7,9-trimethyl-4,13-dioxo-5,12-diazahexadecane-1,16-dioxydimethacrylate (UDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, glycerol dimethacrylate, bisphenol A glycidyl methacrylate (Bis-GMA) and dimethacrylates of dihydroxymethyltricyclo[$5.2.1.0^{2,6}$]decane.

Explicit preference is also given to the corresponding dimethacrylates and diacrylates of dihydroxymethyltricyclo [$5.2.1.0^{2,6}$]decane, as described in the documents DE 1816823, DE 2419887, DE 2406557, DE 2931926, DE 3522005, DE 3522006, DE 3703120, DE 102005021332, DE 102005053775, DE 102006060983, DE 69935794 and DE 102007034457, which by way of reference form part of the present application.

A dental masking compound according to the invention preferably contains one or more acid group-containing light-curable substances. It has been found that no irritation or other damage to the gingiva occurs if small quantities of an acid group-carrying light-curable compound are used. Furthermore, it has been found that the adhesion of a masking compound to the tooth and a tight sealing on the hard substance of the tooth is promoted by the use of one or more acid group-containing monomers in a dental composition according to the invention.

In one preferred dental composition according to the invention, component (a) (ii) contains one or more acid group-containing monomers which have a carboxylic acid function, a phosphoric acid function, a phosphonic acid function, a sulfonic acid function and/or a thiophosphoric acid function, preferably a phosphoric acid function.

The acid group-containing light-curable compound may be a polymerizable monomer which contains one or a plurality of acid functions in a molecule.

Particularly preferred dental compositions according to the invention are characterized in that component (a) (ii) contains
one or more phosphoric acid group-containing monomers selected from the group consisting of 2-(meth)acryloyloxyethyl dihydrogen phosphate, bis-[2-(meth)acryloyloxyethyl] hydrogen phosphate, 2-(meth)acryloyloxyethylphenyl hydrogen phosphate, 6-(meth)acryloyloxyhexyl dihydrogen phosphate, 10-(meth)acryloyloxydecyl dihydrogen phosphate (MDP), 6-(meth)acryloyloxyhexylphenyl hydrogen phosphate, 10-(meth)acryloyloxydecyl dihydrogen phosphate, 1,3-di-(meth)acryloyloxypropane-2-dihydrogen phosphate, 1,3-di-(meth)acryloyloxypropane-2-phenyl hydrogen phosphate and bis-[5-(2-(meth)acryloyloxyethoxycarbonyl) heptyl]hydrogen phosphate,
and/or
one or more carboxylic acid group-containing monomers selected from the group consisting of 4-(meth)acryloxyethyl trimellitic acid (4-MET), 4-(meth)acryloxyethyl trimellitic anhydride (4-META), 4-(meth)acryloxydecyl trimellitic acid, 4-(meth)acryloxydecyl trimellitic anhydride, 11-(meth)acryloyloxy-1,1-undecanedicarboxylic acid, 1,4-di(meth) acryloyloxypyromellitic acid, 2-(meth)acryloyloxyethyl maleic acid, 2-(meth)acryloyloxyethyl phthalic acid and 2-(meth)acryloyloxyethyl hexahydrophthalic acid.

Of the light-polymerizable monomers containing a phosphoric acid group, particular preference is given to 10-(meth) acryloyloxydecyl dihydrogen phosphate (MDP), since particularly good results, in particular very good adhesion values in the sense of the present invention, were achieved with this substance.

The quantity of acid group-containing monomer is preferably selected in such a way that
a) a tight sealing of the tooth neck edge relative to the gingival is achieved,
b) a moderate adhesive effect is achieved, so that the masking compound does not slip when very light (inadvertent) mechanical stress is applied during the treatment, and
c) the material can easily be removed after the end of treatment.

A dental composition according to the invention preferably has a moderate adhesive effect, more preferably an adhesive force of 2-4 MPa, measured on bovine enamel in accordance with the method described in ISO CD 29022.

Further suitable acid group-carrying monomers are mentioned for example in EP 0 980 682 B1 or EP 0 948 955, which by way of reference form part of the present application.

Furthermore, use may also be made of the phosphoric acid esters with glycerol dimethacrylate or with hydroxyethyl methacrylate or with hydroxypropyl methacrylate.

If an acid group-containing monomer of component (a) (ii) is at the same time a dimethacrylate monomer of component (a) (i), it is interpreted for the purposes of the present text as being an acid group-containing monomer of component (a) (ii), particularly in quantitative considerations of the amount of monomer.

Likewise preferred dental compositions according to the invention are characterized in that they contain
component (a) (i) in a quantity of from 42 to 89.5% by weight, preferably in a quantity of from 56 to 79% by weight,
and/or
component (a) (ii) in a quantity of from 0.5 to 8% by weight, preferably in a quantity of from 1 to 4% by weight,
in each case relative to the total weight of the dental composition.

The radically light-polymerizable monomers may also be hydroxyl compounds containing at least one ethylenic double bond. All hydroxyl compounds of acrylates or methacrylates which are conventionally used in dental chemistry may be used. Preference is given to hydroxyl compounds of methacrylates, preferably 2-hydroxyethyl methacrylate, 2-hydroxypropyl methacrylate, 3-hydroxypropyl methacrylate, 1,2-dihydroxy-propyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol dimethacrylate, glycerol dimethacrylate, 2,2-bis-[4-[3-methacryloyloxy-2-hydroxypropoxy]phenyl]propane.

Use may also be made of light-curable monomers with ethylenic double bonds based on polysiloxanes, as described for example in DE 199 03 177 or in DE 44 16 857, which by way of reference form part of the present application.

Said light-polymerizable monomers may be used individually or in mixtures.

Component (b)—Photoinitiators

Examples of a light curing initiator include catalysts which have only a photosensitizing effect and combinations of sensitizers and accelerators.

Examples of photosensitizers are alpha-diketones, benzoin alkyl ethers, thioxanthones, benzophenones, acyl phosphine oxides, acetophenones, ketals, titanocenes, sensitizing dyes, etc. The sensitizers may be used alone or in combination. Specific substance examples of the different classes can be found for example in DE 10 2006 019 092 A1 or in DE 39 41 629 C2, which by way of reference form part of the present application.

Examples of accelerators which are used together with the sensitizers are tertiary amines, secondary amines, barbituric acids, tin compounds, aldehydes and sulfur compounds. Specific substance examples of the different classes can be found in DE 10 2006 019 092 or in DE 39 41 629 C2, which by way of reference form part of the present application.

Further suitable initiators and combinations of initiators are described in DE 601 16 142, which by way of reference forms part of the present application.

The photoinitiators which can be used in the context of the present invention are wherein they can bring about the curing of a composition according to the invention by absorbing light in the wavelength range from 300 nm to 700 nm, more preferably from 350 nm to 600 nm and particularly preferably from 380 nm to 500 nm, optionally in combination with one or more coinitiators.

The absorption maximum of camphorquinone (CQ) is approx. 470 nm and thus in the blue light range. Camphorquinone (CQ) belongs to the $PI_2$ initiators and is often used together with a coinitiator.

Preferably, a masking compound according to the invention contains the combination of an alpha-diketone with an aromatic tertiary amine; preference is given to the combination of camphorquinone (CQ) and ethyl-p-N,N-dimethylaminobenzoate (DABE).

Also preferred is the further combination of the "alpha-diketone/aromatic tertiary amine" system with a phosphine oxide, in particular with phenyl-bis-(2,4,6-trimethylbenzoyl) phosphine oxide and/or 2,4,6-trimethylbenzoyldiphenylphosphine oxide. With regard to the structures of suitable phosphine oxides for use in a composition according to the invention, reference is made to the documents DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which by way of reference form part of the present application.

The phosphine oxides mentioned in said documents are particularly suitable, alone or in combination with the "alpha-diketone/amine" system, as a photopolymerization initiator system in the compositions according to the invention.

As an alternative, the photoinitiators used may also be borate salts, as described for example in U.S. Pat. No. 4,772,530, U.S. Pat. No. 4,954,414, U.S. Pat. No. 4,874,450, U.S. Pat. No. 5,055,372 and U.S. Pat. No. 5,057,393, which by way of reference form part of the present application.

Further suitable photoinitiators are described in J.-P. Fouassier, Photoinitiation, Photopolymerization and Photo-curing, Hanser Publishers, Munich, Vienna, New York 1995 and in J. F. Rabek (ed.), Radiation Curing in Polymer Science and Technology, Vol. II, Elsevier Applied Science, London, New York 1993, which by way of reference form part of the present application.

Component (d)—Polymerization Inhibitors

The dental compositions according to the invention preferably contain one or more inhibitors, also known as stabilizers. These are added to a masking compound in order to avoid spontaneous polymerization. They react with prematurely occurring radicals, which become trapped, prevent premature polymerization and increase the storage stability of the light-curable dental composition. Common inhibitors are phenol derivatives such as hydroquinone monomethyl ether (HQME) or 2,6-di-tert.-butyl-4-methylphenol (BHT). Further inhibitors such as 2,2-diphenyl-1-picrylhydrazyl radicals, galvinoxyl radicals, triphenylmethyl radicals, 2,3,6,6-tetramethylpiperidinyl-1-oxyl radicals (TEMPO) and derivatives of TEMPO or phenothiazine and derivatives of said compound are described in EP 0 783 880 B1, which by way of reference forms part of the present application. Alternative inhibitors are mentioned in DE 101 19 831 A1 or in EP 1 563 821 A1, which by way of reference form part of the present application.

A dental composition which is preferred according to the invention furthermore comprises (d) one or more polymerization inhibitors for increasing the storage stability of the composition, preferably selected from the group consisting of hydroquinone monomethyl ether (HQME), phenols, preferably 2,6-di-tert.-butyl-4-methylphenol (BHT) and tert.-butylhydroxyanisol (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof.

Unlike the molecular weight regulators of component (c), the polymerization inhibitors of component (d) are not capable of H abstraction in the allyl position.

However, if in a specific case a polymerization inhibitor can at the same time be regarded as a molecular weight regulator which is capable of H abstraction in the allyl position, then this is interpreted for the purposes of the present text as being a molecular weight regulator, particularly in quantitative considerations.

The presence of one or more polymerization inhibitors of component (d), preferably BHT and/or TEMPO, in a dental composition according to the invention, particularly in the preferred quantities and quantity ratios mentioned above, is therefore advantageous because the storage stability of a dental composition according to the invention is significantly increased. The effect of the molecular weight regulator(s) (c) of relevance here is not impaired.

A dental composition which is preferred according to the invention comprises component (d) in a quantity of from 10 to 2000 ppm, preferably 50 to 1500 ppm, more preferably 300 to 1000 ppm, in each case relative to the total weight of the dental composition.

If appreciably higher quantities of component (d) are used, the curing of the dental composition is notably slowed.

In further dental compositions which are preferred according to the invention, the ratio of the total weight of component (c) to the total weight of component (d) is greater than 1:1, preferably greater than 2:1, preferably greater than 4:1.

To sum up, such a combination of components (c) and (d), particularly in one of the embodiments referred to as being preferred, ensures, very good storage stability, upon polymerization of the dental composition according to the invention an adjustable/tailored molecular weight distribution after light curing, and an acceptable temperature maximum $T_{max}$ during the photopolymerization of the dental composition in the oral cavity.

Dental compositions according to the invention may also contain fillers. As fillers, use may be made of inorganic glasses or ceramics and/or organic fillers. The fillers may be used alone or as mixtures. In order to optimize the product properties, the fillers may be incorporated in different particle sizes in the recipes. The fillers may have a unimodal or polymodal, for example bimodal, distribution. Use may also be made of materials which have a strengthening effect, such as glass fibers, polyamide fibers or carbon fibers.

The dental composition may additionally contain finely dispersed splitter or bead polymers, wherein the bead polymers may be homopolymers or copolymers of organic curable monomers.

Likewise preferred dental compositions according to the invention are characterized in that they furthermore comprise (e) one or more inorganic components, preferably in a total quantity of from 5 to 40% by weight, more preferably in a total quantity of from 10 to 30% by weight, in each case relative to the total weight of the dental composition.

Suitable inorganic components are for example amorphous materials based on mixed oxides of $SiO_2$, $ZrO_2$ and/or $TiO_2$, microfine fillers such as pyrogenic silica or precipitated silica and macro- or mini-fillers such as quartz glass ceramic or glass powder, barium silicate glasses, barium fluorosilicate glasses, strontium silicate glasses, strontium borosilicate, Li/Al silicate glasses, barium glasses, calcium silicates, sodium aluminum silicates, fluoroaluminum silicate glasses, oxides of aluminum or silicon, zeolites, apatite, zirconium silicates, sparingly soluble metal salts such as barium sulfate or calcium fluoride.

For better incorporation in the polymer matrix, the fillers may be surface-modified. By way of example, mention may be made of the surface treatment of the fillers with a silane. Methacryloxypropyltrimethoxysilane is particularly suitable as the adhesion promoter.

In order to adjust the rheology of the dental masking compounds according to the invention, dental compositions according to the invention may contain different silicas, preferably pyrogenic silicas. Dental compositions according to the invention preferably also contain barium sulfate in order to (further) increase the optical contrast of a dental composition according to the invention with respect to the gums.

In one preferred dental composition according to the invention, the weight ratio of the total quantity of photopolymerizable monomers selected from the group consisting of acrylates and methacrylates (i.e. the photopolymerizable monomers according to component (a) as defined above) to the total quantity of microtine fillers selected from the group consisting of pyrogenic silica and precipitated silica lies in the range from 3:1 to 4:1. In this respect, preference is moreover given to the use of pyrogenic silica. In dedicated experiments, it was found that particularly good rheological properties of a dental composition according to the invention were obtained when a preferred weight ratio was set.

A preferred dental composition according to the invention can be applied by means of a dental syringe.

Preference is given to drip-free syringes (preferably Non-Dripping-Technology (NDT®) syringes), since precise application of a dental composition according to the invention is possible with these and thus it is possible to avoid a disruptive excess of dental composition according to the invention.

A preferred dental composition according to the invention, when applied in the mouth, has a rheological flow behavior and a stability such that no running or spreading of the applied composition takes place.

The viscosity of a dental composition according to the invention is preferably greater than or equal to 10,000 mPas and more preferably lies in the range from 10,000 mPas to 80,000 mPas.

At higher viscosity values, in particular above 90,000 mPas, the flow behavior of the composition becomes much worse and can be pushed out of a conventional dental cannula only with great difficulty.

Preference is given to a dental composition according to the invention having a viscosity of greater than or equal to 15,000 mPas and more preferably greater than or equal to 20,000 mPas.

Very particular preference is given to dental compositions according to the invention having a viscosity in the range from 20,000 mPas to 35,000 mPas, in particular to those dental compositions which at the same time have further preferred material properties, as indicated above or below.

The viscosities mentioned here relate to a measurement at 23° C. using a plate/plate rheometer (diameter of the plate: 25 mm) with a shear rate of 10/sec. and a gap width of 1 mm.

Dental compositions having a viscosity in the very particularly preferred range from 20,000 mPas to 35,000 mPas can be applied to the gingiva in a particularly convenient manner using conventional dental cannulae and in a manner that is pleasant both for the patient and for the treating dentist, without there being any undesired droplet formation or flowing away of the composition. On account of the relatively low viscosity, the applied dental composition covers the gingiva with a precise fit even in the interdental papillae. The preferred dental composition according to the invention does not separate, i.e. the fillers do not separate from the pasty phase.

A preferred dental composition according to the invention is wherein the dental composition, after application to teeth and/or gums, can be transformed by light curing into an elastic material which
  can be pulled off from said teeth or said gums while leaving behind no residue
  and/or
  has a modulus of elasticity<4000 MPa, preferably <2000 MPa, more preferably <1000 MPa.

A preferred dental composition according to the invention is characterized in that, after application to teeth and/or gums, it can be transformed by light curing into a dental elastic material for use in the oral cavity, said material having a modulus of elasticity<4000 MPa, preferably <2000 MPa, very particularly preferably <1000 MPa.

Particular preference is given to a photopolymerizable dental composition according to the invention for application to and for the isolation and protection of gums and/or teeth during dental treatment, comprising:
(a) one or more photopolymerizable monomers selected from the group consisting of acrylates and methacrylates, preferably from the group of the methacrylates,
(b) one or more photoinitiators, preferably selected from the group consisting of alpha-diketones, benzoin alkyl ethers, thioxanthones, benzophenones, acyl phosphine oxides, acetophenones, ketals, titanocenes, borates and sensitizing dyes,
(c) one or more molecular weight regulators selected from the group consisting of compounds which can be reacted with a radical of a monomer of component (a) with abstraction of an H radical from the molecular weight regulator in the allyl position,
and optionally one or more further additives, wherein
the dental composition, after application to teeth and/or gums, can be transformed by light curing into an elastic material which has a modulus of elasticity<1000 MPa.

All of the preferred embodiments mentioned in the present text relate in particular also to this particularly preferred composition.

Preferably, the dental composition according to the invention cannot be transformed by light curing into an elastic material which has a modulus of elasticity>2000 MPa, particularly preferably cannot be transformed into an elastic material which has a modulus of elasticity>1000 MPa.

According to this preferred embodiment, it is not possible, even by intensive irradiation with light, to transform the dental composition into an elastic material of relatively low elasticity.

All of the preferred embodiments mentioned in the present text relate in particular also to this particularly preferred composition.

The modulus of elasticity (bending modulus) is determined from bending tests in accordance with the ISO 4049 standard, average values being formed from 5 individual measurements (3-point bending test; flat/strip sample).

Particularly preferred dental compositions according to the invention have a depth of cure (polymerization depth, DOC) in the range from 1.2 to 2.2 mm, preferably 1.5 to 1.8 mm. The depth of cure is determined in a manner analogous to the ISO 4049 standard with an exposure time of 10 seconds, average values being formed from 3 individual measurements. A depth of cure in the preferred range ensures rapidly achievable protection of the gingiva.

Particularly preferred dental compositions according to the invention can be transformed by light curing into an elastic material which has a bending strength of less than MPa, very particularly preferably less than 47 MPa. The bending strength is determined in accordance with the ISO 4049 standard, average values being formed from 5 individual measurements. According to ISO 4049, therefore, particularly preferred dental compositions according to the invention are not suitable as a restoration material. Preferably, the dental composition according to the invention cannot be transformed by light curing into an elastic material which has a bending strength of more than 50 MPa; with particular preference, the dental composition according to the invention cannot be transformed by light curing into an elastic material which has a bending strength of more than 47 MPa.

To summarize, a dental composition according to the invention, particularly in one of the preferred or particularly preferred embodiments, has the following properties and advantages:

a dental composition according to the invention covers the gingiva right into the interdental spaces, without flowing away (this applies in particular when a viscosity that is referred to above as being preferred is set);

a dental composition according to the invention exhibits a very good flow behavior and good and easy removability after curing;

the released quantity of heat and the associated increase in temperature (up to the temperature maximum $T_{max}$) during the light curing of a dental composition according to the invention is low to moderate and is perceived by many people as being not bothersome or even as being pleasant;

after curing, a dental composition according to the invention does not slip during the treatment and can be removed in one piece after the treatment;

after light curing, a dental composition according to the invention has a particularly low modulus of elasticity, that is to say a particularly high elasticity and flexibility (see above), which distinguishes it from chemically similar compositions of the prior art;

after light curing, a dental composition according to the invention preferably has a particularly low bending strength (see above);

the rheological properties of the dental composition according to the invention are preferably optimized by the presence of microtine fillers (preferably pyrogenic silica) in a suitable quantity (see above) for the intended use according to the invention;

the viscosity of the dental composition according to the invention is preferably set (see above) in such a way that the application thereof to the gingiva using conventional dental cannulae is particularly convenient and is pleasant both for the patient and for the treating dentist, without there being any undesired droplet formation or flowing away of the composition.

Preferably, the proportions of the components in a dental composition according to the invention are selected in such a way that the entire light curing takes place within 20 seconds, more preferably within 10 seconds, per light guide width if the applied layer of the dental composition, given a thickness of 1.5 mm, is irradiated by a 1000 mW/cm$^2$ lamp of a commercially available dental polymerization device.

In one preferred embodiment, a dental composition according to the invention contains no plasticizer and/or no solvent, i.e. no non-reactive organic components. Preferably, a dental composition according to the invention contains no cetyl alcohol.

UV absorbers, which on account of their conjugated double bond systems and aromatic rings are capable of absorbing UV radiation, may optionally be part of a dental composition according to the invention. Examples of UV absorbers are 2-hydroxy-4-methoxybenzophenone, salicylic acid phenyl ester or 3-(2'-hydroxy-5'-methylphenyl)benzotriazole.

For better application control it is advantageous to provide the dental compositions according to the invention in different color shades, which preferably differ appreciably from the color of the gums and/or teeth. For this purpose, use is preferably made of inorganic dyes and/or organic pigments in order to produce a clear contrast for better application control.

Further optional components are flavorings.

The invention also relates to the use of a compound having two or more double bonds which, by abstraction of an allyl H atom, can form a delocalized electron system which extends over 5 or more C atoms of the compound, preferably a diene which, by abstraction of an allyl H atom, can form a delocalized electron system which extends over 5 C atoms, as a molecular weight regulator in the polymerization of monomers selected from the group consisting of acrylates and methacrylates, preferably from the group of the methacrylates, to produce a dental masking compound.

For the kits and methods according to the invention, the details given above in respect of preferred and particularly preferred compositions according to the invention apply accordingly.

For the kits and methods according to the invention, the details given above in respect of preferred and particularly preferred compositions according to the invention apply accordingly, particularly in one of the embodiments indicated as being preferred.

The invention also relates to a kit comprising:

a dental composition according to the invention, and an agent for treating a tooth, which changes a tooth upon contact therewith and/or changes the gum upon contact therewith.

The agent for treating a tooth is an agent which acts indiscriminately both on a tooth which is to be treated and on adjacent teeth and/or gums which are not to be treated when it comes into contact therewith. It must therefore be isolated from adjacent teeth and/or gums.

Preference is given to a kit according to the invention, wherein the agent for treating a tooth is a dental tooth whitening agent.

The invention also relates to a method for producing a protective layer for covering gums and/or teeth and for isolating the gums and/or the teeth from adjacent tooth parts, comprising the following steps:

preparing a photopolymerizable dental composition according to the invention by mixing components (a), (b) and (c) and also optionally component (d) and optionally further components, irradiating the prepared composition with light, so that component (b) initiates the photopolymerization.

The invention also relates to a method for treating one or more teeth, comprising the following steps:

(i) identifying one or more teeth to be treated, (ii) applying a photopolymerizable dental composition according to the invention to the gums or to one or more teeth in the vicinity of the tooth or teeth to be treated, (iii) curing the applied photopolymerizable dental composition under light, (iv) treating the tooth or teeth identified in step (i).

The application of a photopolymerizable dental composition according to the invention is preferably carried out in such a way that the photopolymerizable dental composition according to the invention covers approximately 0.5 mm to 1 mm of the tooth neck of the tooth to be treated. If approximately 0.5 mm of the cervical hard substance of the tooth to be treated is additionally covered with the photopolymerizable dental composition according to the invention, after the curing thereof a particularly effective protection of the gingiva is ensured and the tooth neck is sealed off in a particularly tight manner with respect to the gingiva. Preferably, the photopolymerizable dental composition according to the invention should extend to approx. 3-10 mm over the adjacent gingiva.

A cosmetic (aesthetic) treatment is preferably a treatment for tooth whitening (bleaching), for applying veneers (ceramic covering shells which are adhesively bonded to the tooth) and for applying tooth jewelry (for example fake diamonds, (rhine)stones, images, gold plating or gold foils) to a tooth (also known as dazzlers, twinkles, tooth tattoos, etc.). The cosmetic treatment is preferably a tooth whitening.

The invention also relates to a dental composition according to the invention as a dental masking compound.

The invention also relates to a method of producing a dental masking compound. The method can include: (i) providing a composition comprising monomers selected from the group consisting of acrylates and methacrylates, preferably from the group of the methacrylates; (ii) combining said composition with a molecular weight regulator having two or more double bonds which, by abstraction of an allyl H atom, can form a delocalized electron system which extends over 5 or more C atoms of the compound; and (iii) polymerizing said combination.

The molecular weight regulator can include a diene which, by abstraction of an allyl H atom, can form a delocalized electron system which extends over 5 C atoms. The monomers can include methacrylates.

A method for producing a protective layer is also disclosed. The method can include: (1) preparing a photopolymerizable dental composition described herein by mixing components (a), (b) and (c) and also optionally component (d) and optionally further components, and (2) irradiating the prepared composition with light, so that component (b) initiates photopolymerization of said dental composition.

Finally a method for treating one or more teeth is also disclosed. The method of treating one or more teeth can include: (1) identifying one or more teeth to be treated, (2) applying a photopolymerizable dental composition as described herein to the gums or one or more teeth in the vicinity of the one or more teeth to be treated, (3) curing the applied photopolymerizable dental composition under light, and (4) treating the one or more teeth to be treated. The treatment can be any dental treatment, including cosmetic, preventative, corrective, etc.

The applying step can include applying the dental composition using a syringe. In some examples, the rheological flow behavior and a stability of the applied dental composition is such that no running or spreading of the applied dental composition occurs during the applying step. The method can be such that the cured dental composition can be pulled off the gums or the one or more teeth without leaving a residue behind.

In some methods, the cured dental composition can have a cured thickness in the range from 1.2 to 2.2 mm. The cured dental composition can cover (i) 0.5 to 1 mm of a tooth neck, (ii) 3-10 mm of an adjacent gingiva, or (iii) both.

The invention will be further explained on the basis of the following examples. Unless otherwise indicated, all figures refer to the weight. Use will be made of the following abbreviations which are customary in the field:

BHT=2,6-di-tert.-butyl-4-methylphenol
UDMA=urethane dimethacrylate (7,7,9-trimethyl-4,13-dioxo-5,12-diazahexadecane-1,16-dioxydimethacrylate)
MDP=10-(meth)acryloyloxydecyl dihydrogen phosphate
CQ=camphorquinone
DABE=ethyl-p-N,N-dimethylaminobenzoate
Bis-GMA=bisphenol A glycidyl methacrylate
TEGDMA=triethylene glycol dimethacrylate
4-META=4-methacrylolyoxyethyloxycarbonylphthalic anhydride (4-(meth)acryloxyethyltrimellitic anhydride)
TCD-di-HEMA=bis-(methacrylolyoxymethyl)tricyclo[5.2.1.0$^{2,6}$]decane
HEDMA=1,6-hexanediol dimethacrylate
GlyDMA-phosphate=1,2- and 1,3-glycerol dimethacrylate phosphate
HEMA=hydroxyethyl methacrylate Description of the Methods:

Temperature Maximum ($T_{max}$)

The development of heat during the polymerization was determined using a relative measurement method: a temperature sensor of type L (Fe—CuNi) from the company Reckmann is embedded in a polyethylene holder so that 3 mm of the sensor protrudes. This free end of the temperature sensor is placed centrally in a polyethylene tube having an internal diameter of 3 mm and a height of 5 mm. The tube is filled to the brim with material. A colorless clear acetate film is placed onto the filled tube so that any excess material is compressed. In order to trigger the polymerization, a dental LED lamp with a light output of 1000 mW/cm$^2$ is placed directly onto the acetate film and is switched on for 10 seconds. The change in voltage of the thermoelement resulting from the change in temperature is recorded on an xy plotter L 250-2 from the company Linseis with a sensitivity of 2 mV.

The measurement takes place in a temperature-controlled room at 23° C. and 50% relative humidity under yellow protective light, in order to avoid premature polymerization of the materials. Each individual measurement is started (exposed to light) only after a constant temperature has again been reached after placement of the acetate film and after the measurement plotter has been adjusted to the zero line. The maximum swing of the plotter is measured in scale divisions (0-100 scd). For the sake of clarity, it is noted that the scale divisions (scd) correlate with the temperature (i.e. within one measurement series a higher scd value corresponds to a higher temperature), but do not coincide numerically with ° C. values. The measured values shown are in each case the average values from 3 individual measurements.

$T_{max}$ should preferably be in the range<50 scd, since in such a case the quantity of heat and the temperature were perceived as acceptable or even as pleasant by the persons concerned.

Depth of Cure (DOC)

The depth of cure was determined in a manner analogous to the ISO 4049 standard with an exposure time of 10 seconds. The measured values shown are in each case the average values from 3 individual measurements.

Bending Strength (BS) and Modulus of Elasticity

The bending strength was determined in accordance with the ISO 4049 standard on a material testing machine from the company Zwick. The measured values shown are in each case the average values from 5 individual measurements. The modulus of elasticity (bending modulus) is obtained in a known manner from bending tests in accordance with ISO 4049 (3-point bending test, flat strip sample).

TABLE 1

Compositions containing γ-terpinene as the molecular weight regulator: The quantities shown are parts by weight

|  | Reference | Ex. 1 | Ex. 2 | Ex. 3 | Ex. 4 | Ex. 5 |
|---|---|---|---|---|---|---|
| ethoxylated bisphenol A dimethacrylate | 12.117 | 12.117 | 12.117 | 12.117 | 12.117 | 12.117 |
| UDMA | 60.575 | 60.575 | 60.575 | 60.574 | 60.575 | 60.575 |
| MDP | 2.000 | 2.000 | 2.000 | 1.999 | 2.000 | 2.000 |

TABLE 1-continued

Compositions containing γ-terpinene as the molecular weight regulator:
The quantities shown are parts by weight

|  | Reference | Ex. 1 | Ex. 2 | Ex. 3 | Ex. 4 | Ex. 5 |
|---|---|---|---|---|---|---|
| CQ | 0.146 | 0.146 | 0.146 | 0.146 | 0.146 | 0.146 |
| DABE | 0.219 | 0.219 | 0.219 | 0.219 | 0.219 | 0.219 |
| peppermint flavoring | 1.010 | 1.010 | 1.010 | 1.010 | 1.010 | 1.010 |
| barium sulfate | 2.999 | 2.999 | 2.999 | 2.999 | 2.999 | 2.999 |
| pyrogenic silica | 20.005 | 20.005 | 20.005 | 20.005 | 20.005 | 20.005 |
| blue dye | 0.501 | 0.501 | 0.501 | 0.501 | 0.501 | 0.501 |
| BHT | 0.073 | 0.073 | 0.073 | 0.073 | 0.073 | 0.073 |
| γ-terpinene |  | 0.094 | 0.213 | 0.358 | 0.520 | 0.651 |
| $T_{max}$ [scd] | 64 | 57 | 49 | 43 | 37 | 34 |
| DOC [mm] | 2.03 | 1.91 | 1.72 | 1.63 | 1.45 | 1.32 |

The pyrogenic silica used was Aerosil DT4.

The bending strength (BS) of the masking compound according to Ex. 3 was 17.5 MPa; the adhesive force was 2.8 MPa, measured on bovine enamel in accordance with the method described in ISO CD 29022.

The viscosity of the masking compound according to Ex. 3 was determined at 23° C. using a plate/plate rheometer (diameter of the plate: 25 mm) with a shear rate of 10/sec. and a gap width of 1 mm; the viscosity was 27,000 mPas.

The modulus of elasticity of the masking compound according to Ex. 3 (separate reaction) was 195 MPa after light curing.

TABLE 2

Further exemplary embodiments
The quantities shown are parts by weight

| | | Ex. 6 | Ex. 7 | Ex. 8 | Ex. 9 | Ex. 10 | Ex. 11 |
|---|---|---|---|---|---|---|---|
| Monomers | UDMA | 49.7 | 49.7 | 60.7 | 10.0 | 10.0 | 10.0 |
| | ethoxylated bisphenol A dimethacrylate | 15.0 | 15.0 | 12.0 | 8.0 | 8.0 | 8.0 |
| | TCD-di-HEMA | | | | 15.0 | 15.0 | 15.0 |
| | TEGDMA | 7.3 | 7.3 | | 7.0 | 7.0 | 7.0 |
| | Bis-GMA | | | | 17.0 | 17.0 | 17.0 |
| | HEDMA | | | | 12.0 | 12.0 | 12.0 |
| Acid group-containing monomers | GlyDMA-phosphate | 2.0 | | | | | |
| | MDP | | 2.0 | | | | |
| | di-HEMA-phosphate | | | 2.0 | 1.0 | 1.0 | 1.0 |
| | 4-META | | | | 1.0 | 1.0 | 1.0 |
| | CQ | 0.15 | 0.15 | 0.15 | 0.10 | 0.10 | 0.10 |
| | DABE | 0.22 | 0.22 | 0.22 | 0.14 | 0.14 | 0.14 |
| | barium sulfate | 3.0 | 3.0 | 3.0 | 1.7 | 1.7 | 1.7 |
| | glass ceramic | 5.7 | 5.7 | | 11.0 | 11.0 | 11.0 |
| | pyrogenic silica | 15.0 | 15.0 | 20.0 | 15.0 | 15.0 | 15.0 |
| | dye | 0.50 | 0.50 | 0.50 | 0.50 | 0.50 | 0.50 |
| | BHT | 0.08 | 0.08 | 0.08 | 0.06 | 0.06 | 0.06 |
| | peppermint flavoring | 1.00 | 1.00 | 1.00 | 1.00 | 1.00 | 1.00 |
| Regulators | γ-terpinene | 0.35 | 0.35 | 0.35 | 0.50 | | |
| | 2,4-diphenyl-4-methyl-pentene | | | | | 0.50 | |
| | α-linolenic acid | | | | | | 0.50 |
| | $T_{max}$ [scd] | 44 | 43 | 45 | 41 | 52 | 49 |

TABLE 3

Cetyl alcohol (not according to the invention)
The quantities shown are parts by weight

| | Reference | Ex. 3-1 | Ex. 3-2 | Ex. 3-3 |
|---|---|---|---|---|
| ethoxylated bisphenol A dimethacrylate | 12.117 | 12.117 | 12.117 | 12.117 |
| UDMA | 60.575 | 60.574 | 60.575 | 60.575 |
| MDP | 2.000 | 1.999 | 2.000 | 2.000 |
| di-HEMA-phosphate | 0 | 0 | 0 | 0 |
| CQ | 0.146 | 0.146 | 0.146 | 0.146 |
| DABE | 0.219 | 0.219 | 0.219 | 0.219 |
| peppermint flavoring | 1.010 | 1.010 | 1.010 | 1.010 |
| barium sulfate | 2.999 | 2.999 | 2.999 | 2.999 |
| pyrogenic silica | 20.005 | 20.005 | 20.005 | 20.005 |
| dye | 0.501 | 0.501 | 0.501 | 0.501 |
| BHT | 0.073 | 0.073 | 0.073 | 0.073 |
| cetyl alcohol | | 0.099 | 0.177 | 0.500 |
| $T_{max}$ [scd] | 64 | 61 | 62.5 | 57.5 |

TABLE 4

BHT
The quantities shown are parts by weight

| | Reference | Ex. 4-1 | Ex. 4-2 | Ex. 4-3 |
|---|---|---|---|---|
| ethoxylated bisphenol A dimethacrylate | 12.2 | 12.2 | 12.2 | 12.2 |
| UDMA | 60.6 | 60.6 | 60.6 | 60.6 |
| MDP | 2.0 | 2.0 | 2.0 | 2.0 |
| CQ | 0.146 | 0.146 | 0.146 | 0.146 |
| DABE | 0.219 | 0.219 | 0.219 | 0.219 |
| peppermint flavoring | 1.00 | 1.00 | 1.00 | 1.00 |
| barium sulfate | 3.00 | 3.00 | 3.00 | 3.00 |
| pyrogenic silica | 20.0 | 20.0 | 20.0 | 20.0 |
| dye | 0.50 | 0.50 | 0.50 | 0.50 |
| BHT | | 0.07 | 0.21 | 0.35 |
| $T_{max}$ [scd] | 64 | 61 | 57 | 55 |

TABLE 5

γ-Terpinene without BHT
The quantities shown are parts by weight

| | Reference | Ex. 5-1 | Ex. 5-2 | Ex. 5-3 | Ex. 5-4 | Ex. 5-5 |
|---|---|---|---|---|---|---|
| ethoxylated bisphenol A dimethacrylate | 12.2 | 12.2 | 12.2 | 12.2 | 12.2 | 12.2 |
| UDMA | 60.6 | 60.6 | 60.6 | 60.6 | 60.6 | 60.6 |
| MDP | 2.0 | 2.0 | 2.0 | 2.0 | 2.0 | 2.0 |
| CQ | 0.146 | 0.146 | 0.146 | 0.146 | 0.146 | 0.146 |
| DABE | 0.219 | 0.219 | 0.219 | 0.219 | 0.219 | 0.219 |
| peppermint flavoring | 1.00 | 1.00 | 1.00 | 1.00 | 1.00 | 1.00 |
| barium sulfate | 3.00 | 3.00 | 3.00 | 3.00 | 3.00 | 3.00 |
| pyrogenic silica | 20.0 | 20.0 | 20.0 | 20.0 | 20.0 | 20.0 |
| dye | 0.50 | 0.50 | 0.50 | 0.50 | 0.50 | 0.50 |
| γ-terpinene | | 0.07 | 0.21 | 0.35 | 0.49 | 0.63 |
| $T_{max}$ [scd] | 64 | 60 | 50 | 44 | 39 | 34 |

We claim:

1. A method for application of a photopolymerizable dental composition to and for the isolation and protection of gums during dental treatment, comprising:

applying a photopolymerizable dental composition to a surface of gums of a patient, said photopolymerizable dental composition comprising:
(a) one or more photopolymerizable monomers, wherein component (a) comprises
    (a)(i) one or more dimethacrylate monomers in a quantity of from 42 to 89.5% by weight, and
    (a)(ii) one or more acid group containing monomers in a quantity of from 0.5 to 8% by weight, wherein said one or more acid group containing monomers comprises
        one or more phosphoric acid group-containing monomers selected from the group consisting of 2-(meth acryloyloxyethyl dihydrogen phosphate, bis-[2-(meth)acryloyloxyethyl]hydrogen phosphate, 2-(meth)acryloyloxyethylphenyl hydrogen phosphate, 6-(meth)acryloyloxyhexyl dihydrogen phosphate, 10-(meth)acryloyloxydecyl dihydrogen phosphate (MDP), 6-(meth)acryloyloxyhexylphenyl hydrogen phosphate, 10-(meth)acryloyloxydecyl dihydrogen phosphate, 1,3-di-(meth)acryloyloxypropane-2-dihydrogen phosphate, 1,3-di-(meth)acryloyloxypropane-2-phenyl hydrogen phosphate and bis-[5-(2-(meth)acryloyloxyethoxycarbonyl)heptyl]hydrogen phosphate, and/or
        one or more carboxylic acid group-containing monomers selected from the group consisting of 4-(meth)acryloxyethyl trimellitic acid (4-MET), 4-(meth)acryloxyethyl trimellitic anhydride (4-META), 4-(meth)acryloxydecyl trimellitic acid, 4-(meth)acryloxydecyl trimellitic anhydride, 11-(meth)acryloyloxy-1,1-undecanedicarboxylic acid, 1,4-di(meth)acryloyloxypyromellitic acid, 2-(meth)acryloyloxyethyl maleic acid, 2-(meth)acryloyloxyethyl phthalic acid and 2-(meth)acryloyloxyethyl hexahydrophthalic acid,
(b) one or more photoinitiators,
(c) one or more molecular weight regulators, wherein the one or more molecular weight regulators comprise at least one monoterpene,
(d) one or more polymerization inhibitors for increasing the storage stability of the composition, selected from the group consisting of phenols selected from the group consisting of 2,6-di-tert-butyl-4-methylphenol (BHT) and tert-butylhydroxyanisal (BHA), 2,2-diphenyl-1-picrylhydrazyl radicals, galvinoxyl radicals, triphenylmethyi radicals, 2,3,6,6-tetramethylpiperidinyl-1-oxyl radical (TEMPO) and derivatives thereof, and phenothiazine and derivatives thereof, and
(e) one or more inorganic components in a total quantity of from 5 to 40% by weight, and optionally one or more further additives; and
curing the photopolymerizable dental composition using an irradiation source, wherein the photopolymerizable dental composition comprises:
component (a) in a quantity of from 50 to 90% by weight,
component (b) in a quantity of from 0.01 to 1% by weight,
component (c) in a quantity of from 0.075 to 7.5% by weight, and
component (d) in a quantity of from 10 to 2000 ppm, wherein all weight percentages are relative to the total weight of the dental composition; and
wherein a ratio of the total weight of component (c) to the total weight of component (d) is greater than 1:1,
wherein the application step comprises application by means of a dental syringe.

2. The method as claimed in claim 1, wherein the at least one monoterpene is a monoterpene diene.

3. The method as claimed in claim 1, wherein the at least one monoterpene of component (c) is selected from the group consisting of α-terpinene, β-terpinene, γ-terpinene, α-phellandrene, β-phellandrene and terpinolene.

4. The method as claimed in claim 1, wherein the photopolymerizable dental composition comprises:
component (a) in a quantity of from 60 to 80% by weight,
component (b) in a quantity of from 0.1 to 0.3% by weight, and
component (c) in a quantity of from 0.2 to 0.3% by weight, in each case relative to the total weight of the dental composition.

5. The method as claimed in claim 1, wherein the photopolymerizable dental composition comprises:
component (a) in a quantity of from 60 to 80% by weight,
component (b) in a quantity of from 0.05 to 0.5% by weight, and
component (c) in a quantity of from 0.125 to 3% by weight, in each case relative to the total weight of the dental composition.

6. The method as claimed in claim 1, wherein component (a)(i) contains one or more dimethacrylate monomers selected from the group consisting of ethylene glycol dimethacrylate (EGDMA), 1,6-hexanediol dimethacrylate (HEDMA), triethylene glycol dimethacrylate (TEGDMA), 1,12-dodecanediol dimethacrylate (DODMA), ethoxylated bisphenol A dimethacrylate, polyethylene glycol dimethacrylate (PEGDMA), 7,7,9-trimethyl-4,13-dioxo-5,12-diazahexadecane-1,16-dioxydimethacrylate (UDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol-dimethacrylate, glycerol dimethacrylate, bisphenol A glycidyl methacrylate (Bis-GMA) and dimethacrylates of dihydroxymethyltricyclo[$5.2.1.0^{2,6}$]decane.

7. The method as claimed in claim 1, wherein the photopolymerizable dental composition comprises:
component (a) (i) in a quantity of from 56 to 79% by weight, and/or
component (a) (ii) in a quantity of from 1 to 4% by weight, in each case relative to the total weight of the dental composition.

8. The method as claimed in claim 1, wherein the one or more polymerization inhibitors comprise a phenol selected from the group consisting of 2,6-di-tert.-butyl-4-methylphenol (BHT) and tert.-butylhydroxyanisol (BHA).

9. The method as claimed in claim 1, wherein the ratio of the total weight of component (c) to the total weight of component (d) is greater than 2:1.

10. The method as claimed in claim 1, wherein, during said applying step, said photopolymerizable dental composition has a rheological flow behavior and a stability such that no running or spreading of the applied composition takes place.

11. The method as claimed in claim 1, wherein the, one, a plurality or all of the inorganic components are microfine fillers.

12. The method as claimed in claim 11, wherein the microfine fillers are selected from the group consisting of pyrogenic silica, precipitated silica, and combinations thereof.

13. The method as claimed in claim 12, wherein the weight ratio of the total quantity of photopolymerizable monomers selected from the group consisting of acrylates and methacrylates of component (a) to the total quantity of microfine fillers selected from the group consisting of pyrogenic silica, precipitated silica and combinations thereof lies in the range from 3:1 to 4:1.

14. The method as claimed in claim 1, wherein the at least one monoterpene of component (c) is selected from the group consisting of α-terpinene, β-terpinene, γ-terpinene, and combinations thereof, and the one or more polymerization inhibitor of component (d) is selected from the group consisting of BHT and BHA.

15. The method as claimed in claim 1, wherein the at least one monoterpene of component (c) comprises γ-terpinene, and the one or more polymerization inhibitor of component (d) comprises BHT.

16. The method as claimed in claim 1, wherein dimethacrylate of component (a)(i) comprises 7,7,9-trimethyl-4,13-dioxo-5,12-diazahexadecane-1,16-dioxydimethacrylate (UDMA) and ethoxylated bisphenol A dimethacrylate.

17. The method as claimed in claim 1, wherein component (a)(ii) is present in a quantity of from 0.5 to 4% by weight.

18. The method as claimed in claim 1, wherein:
component (a)(i) comprises 7,7,9-trimethyl-4,13-dioxo-5,12-diazahexadecane-1,16-dioxydimethacrylate (UDMA) and ethoxylated bisphenol A dimethacrylate
component (a)(ii) comprises 10-(meth)acryloyloxydecyl dihydrogen phosphate (MDP);
component (c) comprises γ-terpinene; and
component (d) comprises BHT.

19. The method as claimed in claim 1, wherein the photopolymerizable dental composition comprises:
component (a) in a quantity of from 60 to 80% by weight,
component (b) in a quantity of from 0.05 to 0.5% by weight, and
component (c) in a quantity of from 0.125 to 3% by weight, in each case relative to the total weight of the dental composition.

* * * * *